United States Patent
Kappler et al.

(10) Patent No.: US 8,644,577 B2
(45) Date of Patent: Feb. 4, 2014

(54) METHOD FOR GENERATING IMAGE DATA OF AN OBJECT UNDER EXAMINATION, PROJECTION DATA PROCESSING DEVICE, X-RAY SYSTEM AND COMPUTER PROGRAM

(75) Inventors: Steffen Kappler, Effeltrich (DE); Martin Petersilka, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 43 days.

(21) Appl. No.: 13/435,601

(22) Filed: Mar. 30, 2012

(65) Prior Publication Data
US 2012/0250968 A1  Oct. 4, 2012

(30) Foreign Application Priority Data
Mar. 31, 2011 (DE) .......................... 10 2011 006 579

(51) Int. Cl.
*G06K 9/00* (2006.01)
*A61B 6/00* (2006.01)
*G01N 23/201* (2006.01)

(52) U.S. Cl.
USPC .................................. 382/131; 378/7; 378/86

(58) Field of Classification Search
USPC ......... 382/128, 129, 130, 131, 132, 133, 134; 378/4, 46, 90, 92, 98, 98.4, 98.6, 98.9, 378/101, 140, 7, 70, 86, 901; 128/920, 922
See application file for complete search history.

(56) References Cited

U.S. PATENT DOCUMENTS

| | | | | |
|---|---|---|---|---|
| 7,315,640 B1 * | 1/2008 | Brady et al. | ................... | 382/132 |
| 7,778,384 B2 * | 8/2010 | Proksa | .................. | 378/7 |
| 8,077,826 B2 * | 12/2011 | Ruimi et al. | ...................... | 378/7 |
| 8,150,131 B2 * | 4/2012 | Harer et al. | ................... | 382/131 |
| 2006/0050938 A1 * | 3/2006 | Raupach | ...................... | 382/127 |

FOREIGN PATENT DOCUMENTS

DE   102009048073  B3   7/2011

OTHER PUBLICATIONS

German priority document application No. DE 10 2011 006 579.2 filed Mar. 31, 2011 (not yet published).

* cited by examiner

*Primary Examiner* — Abolfazl Tabatabai
(74) *Attorney, Agent, or Firm* — Harness, Dickey & Pierce, P.L.C.

(57) ABSTRACT

A method is disclosed for generating image data of an object under examination from X-ray projection data of the object under examination, wherein, before a reconstruction of the image data, the X-ray projection data are subjected to scattered radiation correction on the basis of scattered radiation measured values. Here, the scattered radiation measured values are initially subjected to an extra-focal radiation correction before being used for the scattered radiation correction. A projection data processing device is also disclosed for carrying out a method of this kind and an X-ray system, in particular computed tomography system, with a projection data processing device of this kind.

20 Claims, 3 Drawing Sheets

METHOD FOR GENERATING IMAGE DATA OF AN OBJECT UNDER EXAMINATION, PROJECTION DATA PROCESSING DEVICE, X-RAY SYSTEM AND COMPUTER PROGRAM

PRIORITY STATEMENT

The present application hereby claims priority under 35 U.S.C. §119 to German patent application number DE 10 2011 006 579.2 filed Mar. 31, 2011, the entire contents of which are hereby incorporated herein by reference.

FIELD

At least one embodiment of the invention generally relates to a method for generating image data of an object under examination from X-ray projection data of the object under examination, wherein, before a reconstruction of the image data, the projection data are subjected to scattered radiation correction on the basis of scattered radiation measured values. In addition, at least one embodiment of the invention relates to a projection data processing device for carrying out a method of this kind and an X-ray system, in particular a computed tomography system with a projection data processing device of this kind.

BACKGROUND

Methods for scanning an object under examination with a computed tomography system (CT system) are generally known. For example, circular scannings, sequential circular scannings with advance or helical scanning (so-called "spiral scanning") are used for this. With these types of scanning, at least one X-ray source and at least one oppositely located detector record absorption data from the object under examination from different angles and these absorption data or projection data collected in this way are converted by way of corresponding reconstruction methods to form sectional views or three-dimensional volume image data through the object under examination. Computed tomography systems usually use detector systems embodied as a detector array comprising a plurality of X-ray detector elements arranged in rows and columns. Here, the detector system is generally embodied as a partially circular detector, which is arranged opposite to the X-ray source on a so-called gantry and rotates with the gantry or X-ray source. There are also computed tomography systems having a complete detector circuit, wherein the individual X-ray detector elements are read according to the position of the X-ray source.

For the reconstruction of computed tomography images from X-ray CT data records of a computed tomography device (CT device), that is from the acquired projection data, a so-called Filtered Back Projection (FBP) is nowadays employed as the standard method.

In present-day dual-source CT systems (that is CT systems with two or more focus/detector systems), and also in single-source CT systems, with an increasing width of the detector, the greater the significance attached to the scattered radiation in the feed direction, i.e. parallel to the axis of rotation of the X-ray system, (generally referred to as the "z-direction", in which the detector columns—also known as detector channels—extend). In the dual-source CT devices on the market hitherto, attempts are made to compensate the negative influence of the scattered radiation, in particular the cross scatter, on the quality of an image by means of a scattered radiation correction. In principle, with scattered radiation, a differentiation is made between forward scatter and cross scatter.

For detector widths from 4 cm or for quantitative methods, such as those used in particular with, for example, dual energy CT measurements, the scattered radiation correction is based on a measurement of the cross scatter by sensors attached in the z-direction outside the penumbra of the cone beam of the X-ray tube. Typically, there is a row of scattered radiation sensors along both sides of the detector. These scattered radiation sensors can, on the one hand, be conventional detector elements placed outside the useful fan of the X-ray beam (that is outside the detector array used to detect the primary radiation). In some CT systems, on the other hand, dedicated scattered radiation sensors are used outside the main detector. This means that scattered radiation sensors are disposed along the detector on both sides, generally, for each detector module, there is one scattered radiation sensor in the z-direction in front of the main detector and one scattered radiation sensor in the z-direction after the main detector, wherein one detector module in each case encompasses a plurality of detector columns arranged side by side extending in the z-direction.

For an ideal focal spot (e.g. with a rectangular intensity profile), the diaphragm at the tube side can be designed so that only scattered radiation that occurs in the objects to be measured arrives at the scattered radiation sensors and can be measured. However, in reality, the focal spot is surrounded by a low-intensity aureole, a so-called spatially extended halo. This halo is in principle present in all X-ray emitters in which electrons are decelerated in the anode. Unlike the case with the useful focus, the diaphragm close to the tube cannot keep the radiation emerging from this extended halo, the so-called extra-focal radiation completely away from the scattered radiation sensors.

Since this extra-focal radiation superimposed on the scattered radiation also traverses the object to be measured and is ultimately measured in the scattered radiation sensors, this results in unwanted tomography of the regions adjacent to the useful fan. This means that the scattered radiation measured values contain further additional intensities due to the additional tomographic data. Since the scattered radiation correction substantially consists of a subtraction of measured or calculated scattered radiation outside the useful fan, a contrast reversal of these incorrectly additionally measured structures takes place in the reconstructed image data so that a sort of "ghost image" forms. With increasing detector widths in the z-direction, these "ghost image" phenomena represent an increasing problem in particular for dual-source CT systems, since information from ever more remote body regions are projected onto the wrong position.

One reason for this is that with an increasing detector width in the z-direction of the detector, the diaphragm close to the tube also has to have a further aperture in the z-direction. As a result, correspondingly more extra-focal radiation reaches the sensors outside the actual useful fan.

A further parameter influencing the amplitude of the superimposed extra-focal radiation in measurements of scattered radiation with scattered radiation sensors is the distance from the sensor to the penumbra of the focus. For example, the smaller the distance between the sensor and the penumbra, the more extra-focal radiation falls on the sensor. Therefore, the sensors for the measurement of scattered radiation are usually mounted at a sufficient distance from the penumbra. However, with an increasing detector width in the z-direction, in clinical CT, frequently the entire mounting space available to the detector and the scattered radiation sensors plays a role so that, for this reason, a greater distance between the sensors and the detectors would not be favorable.

SUMMARY

At least one embodiment of the invention provides an improved method and an improved projection data processing device for generating image data from X-ray projection data on the basis of an improved scattered radiation correction.

At least one embodiment is achieved by a correction method and at least one embodiment is achieved by a projection data processing device.

With the method according to at least one embodiment of the invention, image data of an object under examination are generated from X-ray projection data of the object under examination, wherein the X-ray projection data are subjected to scattered radiation correction before a reconstruction of the image data on the basis of scattered radiation measured values. According to at least one embodiment of the invention, the scattered radiation measured values are initially subjected to an extra-focal radiation correction, before being used for the scattered radiation correction.

At least one embodiment is directed to a corresponding projection data processing device for processing X-ray projection data of an object under examination initially requires an interface arrangement to accept the X-ray projection data and scattered radiation measured values from a scanner of the computed tomography system. This can be separate interfaces or also a combined interface. In addition, the projection data processing device must have an extra-focal radiation correction unit to correct the measured scattered radiation measured values during an extra-focal radiation correction and a scattered radiation correction unit to correct the X-ray projection data on the basis of corrected scattered radiation measured values during a scattered radiation correction. Finally, the projection data processing device requires a reconstruction unit for the reconstruction of image data of the object under examination on the basis of the corrected X-ray projection data. This can be a conventional reconstruction unit.

At least one embodiment is directed to a computer readable medium including program segments for, when executed on a computer device, causing the computer device to implement the method of at least one embodiment.

BRIEF DESCRIPTION OF THE DRAWINGS

The invention is now described again in more detail in the following with reference to the attached figures describing example embodiments. Here, the same components are given identical reference numbers. The figures show.

Figure 1:
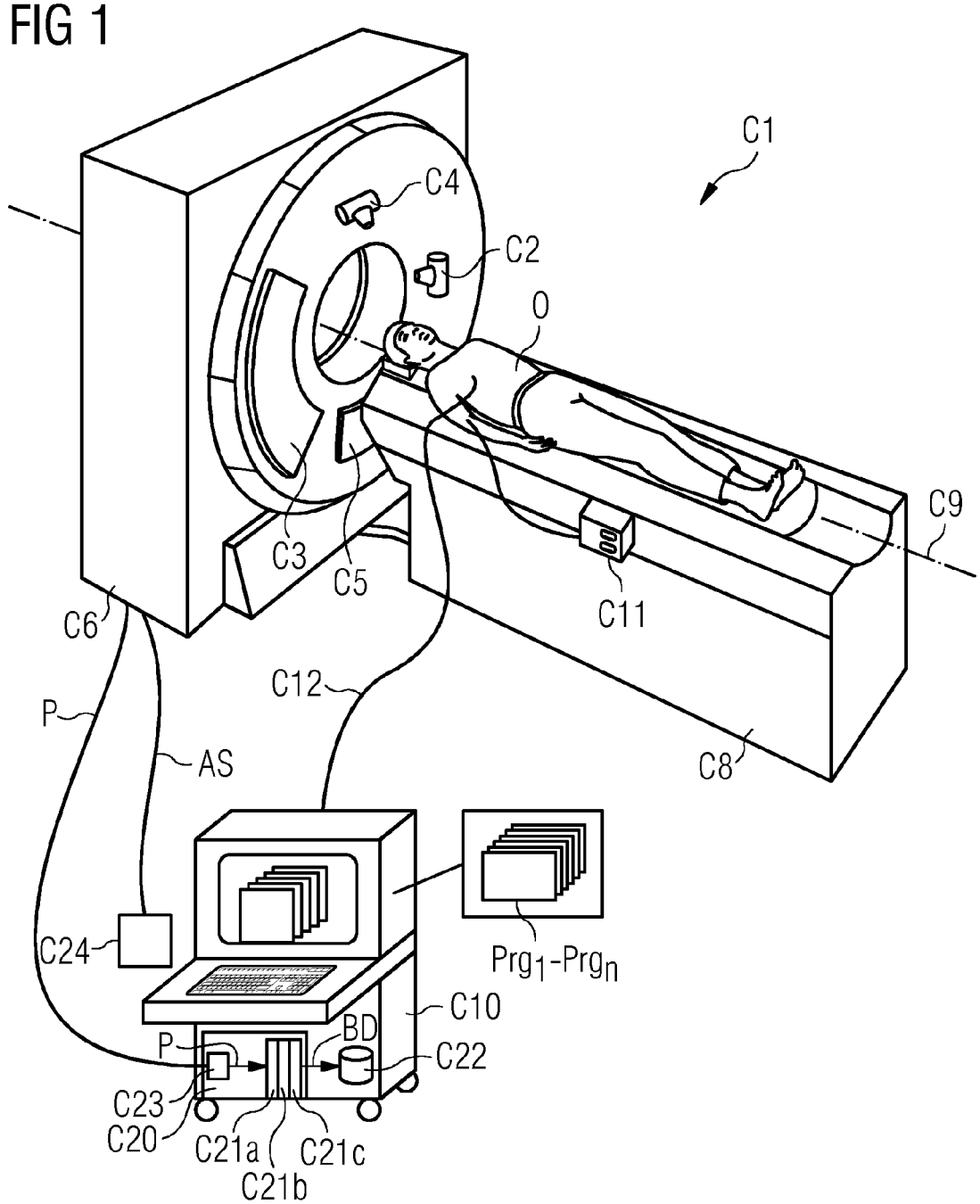
FIG. 1 a schematic representation of an example embodiment of a computed tomography system according to the invention with a projection data processing unit according to the invention and an image reconstruction unit, FIG. 2 a schematic representation of a section of an X-ray tube with extra-focal radiation, FIG. 3 a schematic structure of a detector system constructed from detector modules with scattered radiation sensors, FIG. 4 a flow diagram of an example embodiment of a reconstruction of image data from X-ray projection data using of the extra-focal radiation correction method according to an embodiment of the invention and FIG. 5 a diagram showing an example of coefficients κq of the weighted sum.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

With the method according to at least one embodiment of the invention, image data of an object under examination are generated from X-ray projection data of the object under examination, wherein the X-ray projection data are subjected to scattered radiation correction before a reconstruction of the image data on the basis of scattered radiation measured values. According to at least one embodiment of the invention, the scattered radiation measured values are initially subjected to an extra-focal radiation correction, before being used for the scattered radiation correction.

With this extra-focal radiation correction step, the disruptive extra-focal radiation components contained in the measured scattered radiation measured values are, for example, estimated in order to be able to subtract them from the scattered radiation measured values used thereby before the scattered radiation correction. This improved method in particular enables the tomographic data of the object under examination caused by the extra-focal radiation, which arrive at the scattered radiation sensors and frequently, as explained above, result in so-called "ghost images" during the reconstruction, to be to a large extent eliminated from the measured scattered radiation measured values. The extra-focal radiation correction and the subsequent scattered radiation correction of the projection data can be followed by a reconstruction of the image data, for example using the conventional method.

Particularly preferably, with the method according to at least one embodiment of the invention, the measured scattered radiation measured values are also corrected on the basis of the level of the intensities, i.e. without, for example, performing a conversion to the logarithmic scale frequently used in CT (that is the negative logarithm of the intensity), which is then performed later on the basis of previously corrected X-ray projection data for the reconstruction of the image data. The method according to at least one embodiment of the invention is hence aimed at the distinction between scattered radiation and extra-focal radiation and, not as usual, at the distinction between extra-focal radiation and primary radiation.

At least one embodiment is directed to a corresponding projection data processing device for processing X-ray projection data of an object under examination initially requires an interface arrangement to accept the X-ray projection data and scattered radiation measured values from a scanner of the computed tomography system. This can be separate interfaces or also a combined interface. In addition, the projection data processing device must have an extra-focal radiation correction unit to correct the measured scattered radiation measured values during an extra-focal radiation correction and a scattered radiation correction unit to correct the X-ray projection data on the basis of corrected scattered radiation measured values during a scattered radiation correction. Finally, the projection data processing device requires a reconstruction unit for the reconstruction of image data of the object under examination on the basis of the corrected X-ray projection data. This can be a conventional reconstruction unit.

A projection data processing device according to at least one embodiment of the invention can also be a part of an X-ray system with at least one X-ray source and at least one detector system for the acquisition of projection data records of an object under examination. This means that the projection data processing device can, for example, be installed on a control and evaluation computer of the X-ray system. In principle, however, a projection data processing device of this kind can also be implemented in other computing unit s, which are, for example, connected to an X-ray system of this kind via a network for data acceptance or can be supplied in some other way with corresponding X-ray projection data. The X-ray system is preferably a computed tomography system, since, as mentioned in the introduction, the problem of scattered radiation correction and the occurrence of ghost images due to extra-focal radiation associated therewith is particularly important with this system. However, it can also be a different type of X-ray system, in particular C-arm device with an X-ray source which can be moved relatively slowly around the patient and with a respective suitably positionable detector.

The extra-focal radiation correction unit, the scattered radiation correction unit and the reconstruction unit of the projection data processing device can also be implemented as software modules on a suitable computer. In this case, the computer can contain a program memory for storing program codes, wherein the program memory contains a program code which carries out a method according to at least one embodiment of the invention. The interface arrangement can also be implemented in the form of pure software as long as it is only necessary to accept the data records from, for example, other preprocessing devices or memories implemented on the same computing unit. In principle, however, these interfaces can also be implemented as combined hardware/soft-ware interfaces in order to implement an external acceptance, for example, with the aid of software components of specially configured hardware interfaces.

The projection data processing device usually also has an output interface to output the corrected image data, for example to a suitable memory and/or directly to an operator on a screen or printer. Once again, this output interface can be a pure software interface or a combined hardware/software-interface.

An extensively software-based implementation has the advantage that already existing projection data processing devices can be simply retrofitted by means of a software update in order to work in a manner according to at least one embodiment of the invention. Insofar, the object is also achieved by a computer program product which can, for example, be loaded directly into a memory of a programmable projection data processing device, with program code means encompassing program codes of a computer program in order to carry out all the steps of the correction method according to at least one embodiment of the invention if the computer program is executed in a computer, for example in the projection data processing device.

Further advantageous embodiments and further developments of the invention may be derived from the dependent claims and the following description. Here, the claims of one category can also be further developed in analogy with the dependent claims of another category.

According to an example embodiment of the method according to the invention, as mentioned, during the extra-focal radiation correction, a value representing an extra focal radiation component in the measured scattered radiation measured values can be subtracted from the measured scattered radiation measured values. A value representing the extra focal radiation component is usually a value calculated from a number of measured values, at least one, usually a plurality of measured values, or an estimated value with, depending upon the parameters used, a greater or smaller deviation from the actual extra focal radiation component of the scattered radiation measured value. The more parameters included in the determination of extra focal radiation component to be used for the correction, the more accurately an extra-focal radiation correction for the calculation off corrected scattered radiation measured values can be performed.

Preferably, the scattered radiation measured values are measured by way of a number of scattered radiation sensors, at least one usually a plurality of sensors, and the X-ray projection data are measured by way of detector elements of a projection data detector system. In computed tomography systems, and also in other X-ray systems, as described in the introduction, usually, detector systems are used which are generally constructed from a plurality of detector modules each with a plurality of detectors constructed from a plurality of detector elements, the detectors being partially circular and arranged opposite to the X-ray source and rotating therewith or circular. The detector elements are X-ray sensitive elements, e.g. scintillation elements on which a voltage or a current, usually determined as a function of a collected dose, can be read as a measured value.

The detector elements of a detector module are separated from each other by so-called septums but usually arranged as a firmly connected assembly, for example on a common carrier. However, the person skilled in the art is familiar with the design and mode of operation of detector systems of this kind and therefore they do not need to be explained in detail. Any kind of detector system can be used for the purposes of the invention. For the purpose of at least one embodiment of the invention, scattered radiation sensors should be considered to be any sensors or detectors with which the scattered radiation is to be measured, regardless of whether these are sensor elements especially built as scattered radiation sensors or detector elements of the detector system, for example at edge of the detector system, which are used to measure scattered radiation or reserved for this reason.

During extra-focal radiation correction according to one embodiment of the invention, the extra focal radiation component contained in the measured scattered radiation measured values can be determined from detector measured values of detector elements of the projection data detector system. More precisely, this means that unwanted projection data arriving at the scattered radiation sensor, in particular the tomographic data caused by the extra-focal radiation which has passed through the object under examination, is estimated by means of the detector values measured in the detector elements and then subtracted from the measured scattered radiation measured values for the correction thereof.

It is advantageous to form the extra focal radiation component in a scattered radiation measured value measured with a scattered radiation sensor on the basis of a weighted sum of detector values determined using detector measured values from detector elements which are environmentally adjacent to the scattered radiation sensor in question with the aid of defined total weights κq. Here, "environmentally adjacent detector elements" means detector elements located in a pre-specifiable defined neighborhood of the scattered radiation sensor regardless of whether they are directly or indirectly adjacent thereto, that is, for example, next-but-one neighbors or more remote neighbors of the scattered radiation sensor.

For example, "environmentally adjacent detector elements" can be the detector element directly adjacent to the scattered radiation sensor in the z-direction, the detector elements following this in the z-direction (belonging to the same detector channel k) or even the detector elements lying perpendicular to these detector elements, i.e. from directly adjacent detector channels k=k−1 or k=k+1 or detector channels with a spacing-apart of one or more channels (e.g. k=k−2, k=k−1, k=k+1, k=k+2). Here, it is possible to prespecify in each case the depth in the z-direction to which the detector elements or how many detector channels count as the "environment" of a scattered radiation sensor.

As explained above, the scattered radiation sensors are usually arranged along or next to an edge of the projection data detector system. For example, this can be implemented either by sensors in the edge rows of a multi-row detector or a planar detector located outside the set useful fan or by dedicated sensors with the greatest different spatial scanning compared to the main detector. The weighted sum for determining the extra focal radiation component in a scattered radiation measured value measured with this scattered radiation sensor can then preferably be formed on the basis of detector values determined using detector measured values of a number of detector elements, which are arranged in relation to the scattered radiation sensor in question in a direction lying along an edge extending perpendicular to the edge of the projection data detector system, that is the so-called z-direction.

To be more precise, preferably the disruptive extra-focal radiation components in the measured scattered radiation measured values $m(\zeta,l,r)$ are determined for each sensor channel l in the sensor row $\zeta$ and for each focus position r using a weighted sum from the measured scattered radiation measured value $m(\zeta,l,r)$, i.e. the intensity arriving at the scattered radiation sensor and a series of detector measured values $\tilde{s}(l,q,r)$ of the intensity arriving at the detector for different detector rows q=1 to q=Nk and then subtracted from the measured scattered radiation measured value in order to obtain the corrected scattered radiation measured values $m_{corr}(\zeta,l,r)$:

$$m_{corr}(\zeta, l, r) = m(\zeta, l, r) \cdot \kappa_1(\zeta, r) + \sum_{q=2}^{N_k} \kappa_q(\zeta, r) \cdot \tilde{s}(l, q, r) \quad (1)$$

Here:
$m_{corr}(\zeta,l,r)$=corrected scattered radiation measured values
$m(\zeta,l,r)$=measured scattered radiation measured values
$\tilde{s}(l,q,r)$=detector values
$\kappa_1(\zeta,r)$=weighting factor for q=1
$\kappa_q(\zeta,r)$=total weights
$\zeta$=sensor row
l=sensor channel
q=detector row
r=focus position on the X-ray tube Here, the total weights $\kappa_q(\zeta,r)$ are dependent upon the focus position r and the sensor row $\zeta$, wherein the focus position r is only a logical value for the actual focus position when using an X-ray tube with spring focus and the sensor row $\zeta$ can indicate whether the scattered radiation sensor is located in the z-direction before or behind the detector. As mentioned above, Nk is the number of detector elements to be taken into account in the z-direction, i.e. this value delimits the above-described "neighborhood" of the detector elements to be taken into account in the z-direction. When specifying this number Nk, preferably care is taken to ensure a suitable compromise between accuracy and the computing time required. In order to achieve an expedient quality of the extra-focal radiation correction, for a detector with a total of 64 rows, it is possible, for example, to use up to 32, preferably up to 16, for example, the 1st to 10th adjacent detector value in the z-direction, for the weighted sum, i.e., for a detector with 64 rows, Nk is preferably smaller than or equal to 32, preferably smaller than or equal to 16, but at least 10. The total weights $\kappa_q(\zeta,r)$ are negative values and the weighting factor $\kappa_1(\zeta,r)$ is positive so that, as desired, the weighted sum of detector values $\tilde{s}(l,q,r)$ is subtracted from the measured scattered radiation measured value $m(\zeta,l,r)$.

Advantageously, here, the correction described is performed in the column direction of the detector (i.e. within the same channel or in the z-direction) with asymmetric total weights $\kappa_q$. The detector values $\tilde{s}(l,q,r)$ refer to detector channels with the index k, which belong to the same value of the fan angle of the useful fan as the scattered radiation sensor of the channel with the value l.

The measured values $m(\zeta,l,r)$ represent the radiation intensity arriving at the sensor location. Since the sensor is located outside the useful fan (i.e. detector module), this measured variable represents an approximate of the scattered radiation intensity present in the useful fan. The reason for this is inter alia the fact that the scattered radiation propagates in the form of spherical waves, to be precise from the scattering centers located in the useful fan. Contrary thereto, the intensity arriving at the detector, i.e., in addition to the scattered radiation, the detector measured values within the useful fan also contain the direct radiation, which is attenuated going from the tube focus through the object. In the extra-focal radiation correction, the measured values are preferably processed at the level of the intensities.

The above-described detector values in connection with equation (1) $\tilde{s}(l,q,r)$ can in principle be detector measured values of the detector elements of a channel (in the z-direction). However, in a further preferred variant, the detector values are formed on the basis of detector measured values of a number of detector elements lying parallel to the edge (i.e. each in one row of the detector). Particularly preferably, the formation of a mean value from detector measured values from a plurality of channels enables the use of a broad base of measured values, in particular with respect to an improved signal-to-noise ratio in order to improve the extra-focal radiation correction. The following equation (2) is an example of a possibility for determining a detector value $\tilde{s}(l,q,r)$ by means of a mean value determination from detector measured values $s(k,q,r)$ always for four adjacent channels (k=6 to 9 in each case), when, for example, as in this case, a detector is used with detector modules each comprising 16 channels and with which, for each detector module, one scattered radiation sensor is used in each case for the right and left (viewed in the z-direction, in front and behind):

$$\tilde{s}(l,q,r) = \frac{1}{4} \sum_{k=16l+6}^{16l+9} s(k,q,r) \quad (2)$$

This averaging is, for example, performed separately for each projection angle (i.e. for each tube position). Equation (2) can be used directly in equation (1).

When the scattered radiation sensor is arranged at a distance from the edge of the projection data detector system, for example in order to lie outside the penumbra of the focus, there is a further difficulty in the absence of measured data in the region of the gap between the detector edge and sensor row. These sensor rows typically lie up to about 2 cm, preferably up to about 1 cm, outside the useful fan and hence are remote from the nearest detector elements. However, the results show that these missing data can be interpolated in good approximation linearly between the scattered radiation measured value and the most extreme, i.e. directed on the edge toward the scattered radiation sensor, detector element of the first detector row. This means that the detector array matrix can be supplemented by a number of rows Nvirt., i.e. at least one, but usually more rows, on "virtual detector elements" in order to fill the gap between the edge of the useful fan with detector elements and the sensor element appropriately with these virtual detector elements. In the case of extra-focal radiation correction, it is then possible to take into account interpolated and/or extrapolated detector values in the weighted sum representing detector measured values of a number of virtual detector elements arranged between the scattered radiation sensor and the edge of the projection data detector system. Equation (1) is then changed as follows:

$$m_{corr}(\zeta,l,r) = m(\zeta,l,r) \cdot \kappa_1(\zeta,r) + \sum_{q=2}^{N_{virt}+1} \kappa_q(\zeta,r) \cdot s^{virt}(l,q,r) + \sum_{q=N_{virt}+2}^{N_k} \kappa_q(\zeta,r) \cdot \tilde{s}(l,q,r) \quad (3)$$

The detector values $s^{virt}(l,q,r)$ of these "virtual detector elements" can be determined by interpolation or by extrapolation from the "genuine" detector measured values (e.g. the detector values $\tilde{s}(l,q,r)$ of the corresponding column in the z-direction).

In order to ensure that a negative corrected scattered radiation measured value is never taken into account in the scattered radiation correction, preferably, with the scattered radiation correction, a corrected scattered radiation measured value with a value 0 is assumed when the scattered radiation measured value in question has a negative value after an extra-focal radiation correction. For this, equation (3) can be modified as follows:

$$m_{corr}(\zeta,l,r) = \max\left(0, m(\zeta,l,r) \cdot \kappa_1(\zeta,r) + \sum_{q=2}^{N_{virt}+1} \kappa_q(\zeta,r) \cdot s^{virt}(l,q,r) + \sum_{q=N_{virt}+2}^{N_k} \kappa_q(\zeta,r) \cdot \tilde{s}(l,q,r)\right) \quad (4)$$

In a corresponding way, equation (1) can also be modified when no virtual detector rows are to be taken into account.

Preferably, before the subtraction for the extra-focal radiation correction, the measured scattered radiation measured values $m(\zeta,l,r)$ are multiplied with a positive weighting factor $\kappa_1(\zeta,r)$ in order to satisfy the boundary condition such that the sum of all weighting factors should be equal to 1, i.e. that the following boundary condition is satisfied:

$$\sum_q \kappa_q = 1 \quad (5)$$

This ensures the correct normalization of the correction, e.g. in the (hypothetical) case of an exactly homogeneous radiation field in the z-direction, the original sensor measured value must be reproduced, after executing the weighted sum.

In an example embodiment of the method according to the invention, for a computed tomography system, beforehand a number of, at least one, generally but also more, different sets of total weights $\kappa q$ have to be provided for the extra-focal radiation correction. Here, depending upon the parameter combination, different sets of total weights are obtained in each case. These total weights can be determined with the aid of test measurements on the computed tomography system in question or a computed tomography system of a suitable type.

Figure 5:
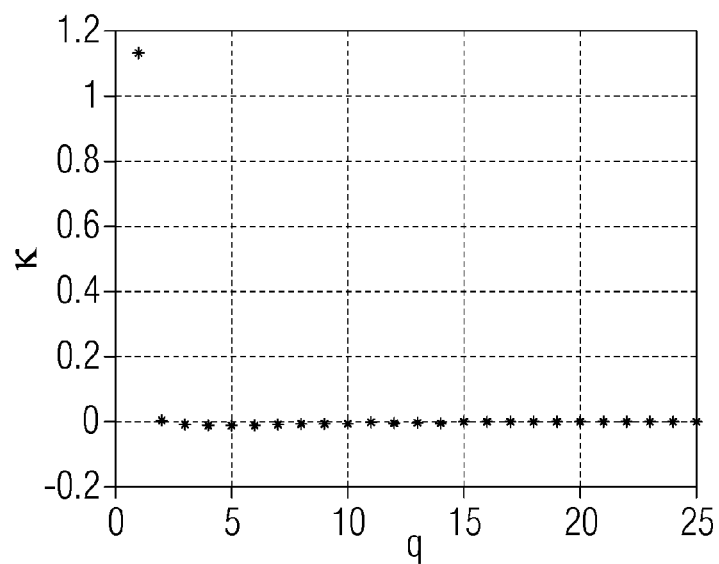

To determine the total weights $\kappa q$, they can, for example, initially be determined empirically. FIG. 5 shows an example of a set of total weights. An empirical determination of this kind can advantageously be estimated using the measurement of the impulse response of the extra-focal radiation in the z-direction, e.g. via an independent second detector and inversion of the pulse response (e.g. by the Fourier transformation, inversion and then the inverse Fourier transformation). The resultant function of q obtained is symmetrical total weights with respect to q=1.

Then, the first values for the total weights κq obtained can be varied until, after scattered radiation correction and reconstruction of the image data from the corrected scattered measured values, reconstructed images of measuring phantoms and images of patient scans no long contain any visible "ghost images". Here, the total weights for q<1 are set constantly to zero and the summation only covers the positive indices (including 1), i.e. only the weights for q>1 are varied. The total weight for q=1 is obtained from boundary condition stated in equation (4) that the sum of all total weights should be equal to 1.

Hereby, the values of the total weights are additionally also dependent upon the observed sensor row ζ because the extra-focal radiation does not have to be symmetrical in the z-direction but is advantageously asymmetric. In addition, the total weights can be dependent on the focus position r and/or the tube voltage and/or the opening width of a tube-side collimator of the X-ray source. Depending upon the parameter combination, this results in different sets of total weights. These total weights can then be determined firmly for a scanner type and are then no longer changed within the scope of the extra-focal radiation correction of the scattered radiation measured values.

FIG. 1 is a schematic diagram of a computed tomography system C1 with an image reconstruction device C21c. A gantry housing C6 contains a gantry (not shown here) on which are arranged a first X-ray tube C2 and an opposite detector C3. Optionally, the CT system shown here has a second X-ray tube C4 with an opposite second detector C5 so that the additionally available emitter/detector combination enables a higher time resolution to be achieved or, when different X-ray energy spectra are used in the emitter/detector systems, also enables the performance of "dual-energy" examinations.

The CT system C1 also has a patient couch C8 on which, during the examination, a patient or an object under examination O can be moved along a system axis C9, also called the z-axis into the measuring field, wherein the scanning itself can also be performed as a pure sequential circular scan without advancing the patient exclusively in the examination area of interest. Here, the respective X-ray source C2 or C4 rotates about the patient. In parallel to this, the X-ray source C2 or C4 follows the detector C3 or C5 in order to acquire the X-ray projection data P, which can then be used for the reconstruction of slice images. Alternatively to a sequential scan of this kind, with which the patient is moved gradually between the individual scans through the examination field, it is obviously also possible to perform a helical scan (often called "a spiral scan"), with which, during the rotating scanning with the X-radiation, the patient is moved continuously along the system axis C9 through the examination field between X-ray tube C2 or C4 and detector C3 or C5. With a spiral scan, moving the patient along the axis C9 and the simultaneous rotation of the X-ray source C2 or C4 results in a helical path for the X-ray source C2 or C4 relative to the patient during the measurement. This path can also be achieved by moving the gantry along the axis C9 with a motionless patient.

The CT system C1 is controlled by a control and computing unit C10, with computer program code Prg1 to Prgn existing in a memory. The control and computing unit C10 can be used to transmit acquisition control signals AS via a control interface C24 in order to control the CT system C1 according to specific measuring protocols.

The control and computing unit C10 here comprises inter alia a projection data processing unit C20 according to the invention. The projection data P acquired by the detector C3 or C5 are transmitted via an interface arrangement C23 for accepting the projection data P and scattered radiation measured values, which can be embodied as one or two separate interfaces, to the projection data processing unit C20. The scattered radiation measured values are corrected using detector measured values, i.e. individual values of the projection data, in an extra-focal radiation correction unit C21a within the scope of an extra-focal radiation correction, as described above and below. The X-ray projection data P are then, optionally after suitable preprocessing, corrected in a scattered radiation correction unit C21b of the projection data processing unit C20 within the scope of a scattered radiation correction using the corrected scattered radiation measured values and further processed in an image reconstruction unit C21c, i.e. image data BD are reconstructed therefrom. With this exemplary embodiment, the correction- and image reconstruction units C21a, 21b, 21c are implemented as parts of the projection data processing unit C20 in the form of software on a processor in the control and computing unit C10, e.g. in the form of one or more of the computer program codes Prg1 to Prgn. The image data BD reconstructed by the image reconstruction unit C21c are then stored in a memory C22 of the control and computing unit C10 and/or output on the screen of the control and computing unit C10 in the usual way. They can also be fed via an interface (not shown in FIG. 1) into a network connected to the computed tomography system C1, for example a radiology information system (RIS), and stored in a mass memory accessible there or output as images.

The control and computing unit C10 can additionally also perform the function of an EKG, wherein a lead C12 is used to lead off the EKG potentials between the patient and projection data processing unit C20. Additionally, the CT system C1 shown in FIG. 1 also comprises a contrast agent injector C11, via which additionally a contrast agent can be injected into the patient's blood circulation thus enabling a better depiction of the patient's vessels, in particular the ventricles of the beating heart.

Figure 2:
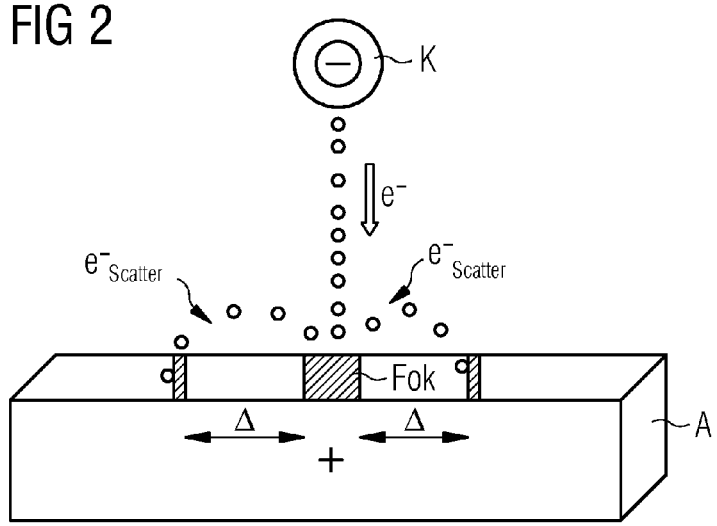

FIG. 2 is a schematic representation of a section of an X-ray tube with extra-focal radiation, such as can be used in the CT system in FIG. 1. The X-radiation emitted by the X-ray tube is generated in that electrons e– emitted by a hot cathode K are accelerated with a high voltage present between cathode K and anode A. When the high-speed electrons e– enter the anode material, e.g. tungsten, X-radiation is produced. This mainly corresponds to the bremsstrahlung of the electrons e–.

The definition of the reconstructed images substantially depends on the size of the focal spot on the anode A of the X-ray tube. The useful focal spot Fok, that is the region of the anode A, which emits the majority of the X-radiation, is known as the useful focus. With diagnostic X-ray tubes, focal spot dimensions of between 0.3 mm and 2 mm are usual. Depending upon the design of the X-ray tube, X-radiation can emerge outside the actual useful focus over a region of several centimeters, which hence helps to impair the contrast of the image.

This parasitic X-radiation is known as extra-focal radiation, abbreviated to EFR, also known as: off-focus radiation). The formation of EFR can be explained as follows: some of the electrons e– arriving at the anode A at a high speed are either scattered back elastically by the anode A or they trigger secondary electrons in the anode A, which leave the anode surface again. The energy of these scattered primary or secondary electrons e-Scatter is reduced by about 20% compared to the energy of the primary electrons e–. The electrons e-Scatter are attracted by the electrical field of the anode A and arrive once again at anode A. The X-radiation generated by these electrons e-Scatter is the extra-focal radiation. Due to the preceding loss of energy of the electrons e-Scatter, the EFR is on average softer than the focal X-radiation. Here, the point of impact of the scattered electrons e-Scatter is usually remote from the actual useful focal spot Fok. The electrons e-Scatter enlarge the emission zone and hence the imaging radiation source and result in a widening of the useful focal spot Fok. In FIG. 2, this is indicated by the distances Δ next to the useful focal spot Fok. Depending upon the design of the X-ray tube, the proportion of the EFR in the entire radiation emitted by the X-ray tube is typically up to about 10%.

Figure 3:
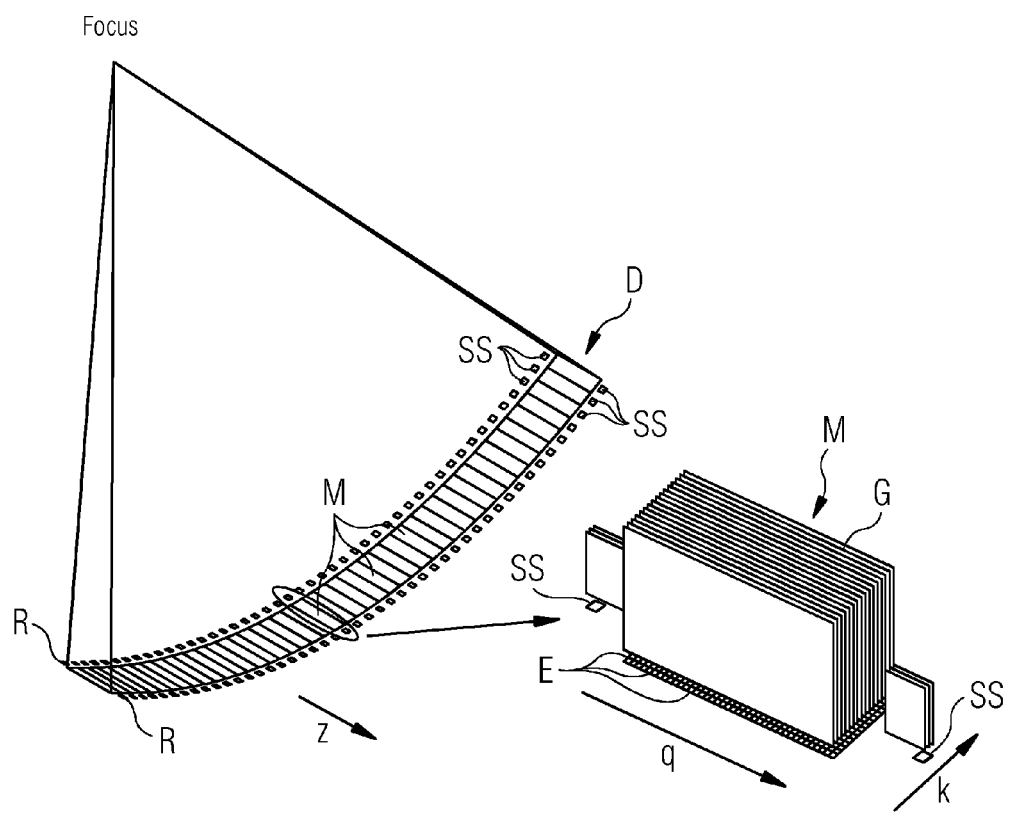

FIG. 3 shows the schematic structure of a projection data detector system D (hereinafter abbreviated to detector D) with a plurality of detector modules M, each constructed from a plurality of detector elements E arranged next to each other in a matrix shape in rows q and columns (=detector channels) k (here, the arrows in the diagram indicate the direction in which the rows q or columns k are arranged next to each other). The detector D is arranged in a partially circular shape in a gantry (not shown) opposite the X-ray tube, wherein, in this diagram, only the focus position F of the X-ray tube and the useful fan of the X-radiation are schematically indicated. Each of the detector modules M here comprises a plurality of detector channels in the z-direction (i.e. in the direction, in which the columns k extend). Along the useful fan or the detector D, on both sides of each detector module M, i.e. in the z-direction in front of and behind the detector module M, there is in each case a scattered radiation sensor SS at a distance from the edge R of the detector D. The scattered radiation sensors SS can, on the one hand, be conventional detector elements placed outside the useful fan, but can also be dedicated scattered radiation sensors.

The enlarged diagram on the right side of the diagram shows the structure of a detector module M with scattered radiation sensors SS. The pixels or detector elements E of the detector D lie in the center of the module M and to the side of these in each case the scattered radiation sensors SS. In FIG. 3, with for example, 16 detector channels of a detector module M, a scattered radiation sensor SS is arranged both in front of and behind the detector module M in the z-direction. A further scattered radiation grid G is provided over the active detector and sensor surfaces in order to filter out the scattered radiation perpendicularly or transversely to the z-direction, i.e. in the circumferential direction or row direction of the detector D or the gantry as soon as possible before it arrives at the detector elements E and scattered radiation sensors SS.

Figure 4:
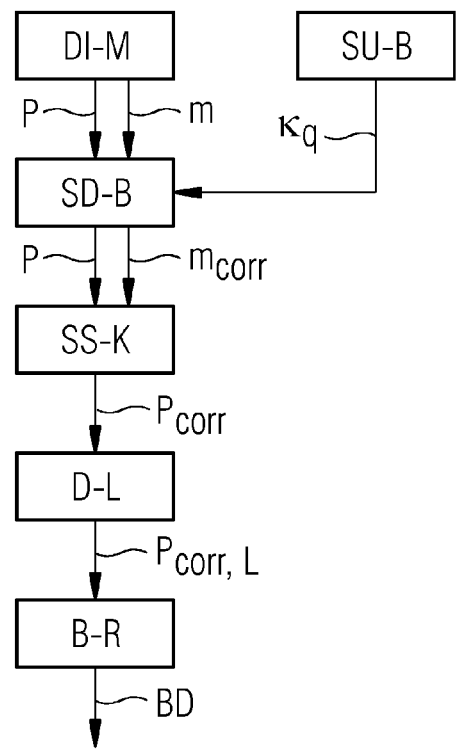

FIG. 4 is a schematic representation of a flow diagram of an example embodiment of a method for the determination of image data from the X-ray projection data using the correction method according to an embodiment of the invention comprising the following steps:

DI-M: measuring the signal intensities on the detector in the useful fan, i.e. the detector measured values s(k,q,r), which are also simultaneously the X-ray projection data P, and the signal intensities on the scattered radiation sensors SS, i.e. the scattered radiation measured values m(ζ,l,r), for each projection angle, SU-B: determination of the total weights κq, as a function of the sensor row, focus position, tube voltage and collimation, SD-B: Performance of the extra-focal radiation correction, i.e. calculation of the corrected scattered radiation measured values mcorr, SS-K: performance of the scattered radiation correction of the X-ray projection data using the corrected scattered radiation measured values mcorr, D-L: taking the logarithm of the corrected projection data Pcorr, B-R: reconstruction of image data BD by means of the logarithmized corrected projection data Pcorr,L.

In the first step DI-M, the signal intensities on the detector in the useful fan, i.e. the detector measured values s(k,q,r) (hereinafter also called projection data P), and the signal intensities on the scattered radiation sensors, i.e. the measured scattered radiation values m(ζ,l,r), are measured for every projection angle. This projection data P and scattered radiation measured values m are then, optionally following suitable preprocessing, sent to a projection data processing unit C20 by means of suitable interfaces.

In a step SU-B, the total weights are also selected as a function of the sensor row, focus position, tube voltage and collimation and sent to an extra-focal radiation correction unit C21a or already stored therein beforehand. The determination of these total weights κq is performed, as described above with reference to equation (5), in advance for the respective computed tomography scanner or design.

In a further step SD-B, at the level of the signal intensities, a correction of the scattered radiation measured values m is performed within the scope of an extra-focal radiation correction as described above, for example, with reference to equations (1) to (4), wherein the calculation of the corrected scattered radiation measured values mcorr with a detector D according to FIG. 3 is preferably performed by means of equation (4) since the scattered radiation sensors SS are located at a distance from the edge R of the detector D.

In the next step, a scattered radiation correction (SS-K) is then performed in the scattered radiation correction unit C21b with the aid of the previously corrected scattered radiation measured values mcorr, before the corrected X-ray projection data Pcorr generated in this are then, as is usual, logarithmized in a step D-L. Finally, image data BD are reconstructed from the logarithmized corrected X-ray projection data Pcorr,L (in the step B-R) by means of the image reconstruction unit C21c.

FIG. 5 is a diagram showing an example of coefficients κq of the weighted sum, in which the total weight K1 (where q=1), i.e. the weighting factor for the measured scattered radiation measured value is about 1.15, i.e. represents a positive value. The total weights κq where q=2-25 are less than zero. They are between about 0-0.1.

Finally, reference is made again to the fact that the correction method described in detail above and the projection data processing device and the X-ray system presented are only example embodiments, which the person skilled in the art could modify in a wide variety of ways with departing from the scope of the invention. For example, the CT system can also be a C-arm system, in which, unlike the CT system in FIG. 1, the housing bears a C-shaped arc, i.e. a so-called C-arm, with an X-ray tube attached to one side and an opposite detector on the other side. In addition, the correction method can in principle also be used with other CT systems, e.g. for CT systems with a detector forming a complete ring. In addition, the use of the singular indefinite article does not exclude the possibility that the features in question could also occur several times. In addition, "units" can comprise one or more, also spatially distributed components. Similarly, a "device" can comprise a component or also a plurality of components.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating image data of an object under examination based on X ray projection data of the object under examination, the method comprising:
subjecting the X-ray projection data, before a reconstruction of the image data, to scattered radiation correction based on scattered radiation measured values, wherein the scattered radiation measured values are initially subjected to an extra-focal radiation correction before being used for the scattered radiation correction.

2. The method as claimed in claim 1, further comprising:
subtracting, from the scattered radiation measured values, a value representing an extra focal radiation component in the scattered radiation measured values during the extra-focal radiation correction.

3. The method as claimed in claim 2, wherein, before the subtraction, a scattered radiation measured value is multiplied by a positive weighting factor.

4. The method as claimed in claim 2, wherein the scattered radiation measured values are measured by a number of scattered radiation sensors and the X-ray projection data are measured by detector elements of a projection data detector system, and wherein the extra focal radiation component contained in the scattered radiation measured values is determined from detector measured values of the detector elements of the projection data detector system.

5. The method as claimed in claim 4, wherein the extra focal radiation component is formed in a scattered radiation measured value measured with a scattered radiation sensor based on a weighted sum of detector values determined based on detector measured values from detector elements adjacent to the scattered radiation sensor in an environment with the aid of defined total weights.

6. The method as claimed in claim 1, wherein the scattered radiation measured values are measured by a number of scattered radiation sensors and the X-ray projection data are measured by detector elements of a projection data detector system, and wherein an extra focal radiation component contained in the scattered radiation measured values is determined from detector measured values of the detector elements of the projection data detector system.

7. The method as claimed in claim 6, wherein the extra focal radiation component is formed in a scattered radiation measured value measured with a scattered radiation sensor based on a weighted sum of detector values determined based on detector measured values from detector elements adjacent to the scattered radiation sensor in an environment with the aid of defined total weights.

8. The method as claimed in claim 7, wherein for an X-ray system, a number of different sets of total weights are provided for the extra-focal radiation correction.

9. The method as claimed in claim 8, wherein the total weights are determined with the aid of test measurements on a computed tomography system in question or a computed tomography system of a suitable type.

10. The method as claimed in claim 7, wherein the total weights are determined as a function of a sensor row.

11. The method as claimed in claim 10, wherein the total weights are determined as a function of the sensor row and as a function of at least one of a focus position, a tube voltage and an opening width of a tube-side collimator of an X-ray source.

12. The method as claimed in claim 6, wherein a scattered radiation sensor is arranged on or next to an edge of the projection data detector system and a weighted sum for determining the extra focal radiation component is formed in a scattered radiation measured value measured with the scattered radiation sensor based on detector values, which are formed using detector measured values from a number of detector elements, which are arranged respective to the scattered radiation sensor in a direction extending along a direction perpendicular to the edge of the projection data detector system.

13. The method as claimed in claim 12, wherein the detector values are formed using a number of detector elements arranged in parallel with the edge from detector measured values.

14. The method as claimed in claim 13, wherein the scattered radiation sensor is arranged spaced apart from the edge of the projection data detector system and at least one of interpolated and extrapolated detector values in the weighted sum are taken into account, which represent detector measured values of a number of virtual detector elements arranged between the scattered radiation sensor and the edge of the projection data detector system.

15. The method as claimed in claim 12, wherein the scattered radiation sensor is arranged spaced apart from the edge of the projection data detector system and at least one of interpolated and extrapolated detector values in the weighted sum are taken into account, which represent detector measured values of a number of virtual detector elements arranged between the scattered radiation sensor and the edge of the projection data detector system.

16. The method as claimed in claim 1, wherein a corrected scattered radiation measured value of 0 is assumed for the scattered radiation correction when the scattered radiation measured value in question has a negative value after an extra-focal radiation correction.

17. A non-transitory computer readable medium including computer executable program instructions that, when executed on a computer device, cause the computer device to implement the method of claim 1.

18. A projection data processing device for processing X-ray projection data for an object under examination, the method comprising:
 an interface arrangement to accept the X-ray projection data and scattered radiation measured values;
 an extra-focal radiation correction unit to correct the scattered radiation measured values within the scope of an extra-focal radiation correction;
 a scattered radiation correction unit to correct the X-ray projection data based on corrected scattered radiation measured values within the scope of a scattered radiation correction; and
 a reconstruction unit to reconstruct image data for the object under examination based on the corrected X-ray projection data.

19. An X-ray system, comprising:
 at least one X-ray source; and
 at least one detector system to acquire X-ray projection data of an object under examination; and
 a projection data processing device as claimed in claim 18.

20. The X-ray system of claim 19, wherein the X-ray system is a computed tomography system.

* * * * *